(12) United States Patent
Clark

(10) Patent No.: US 7,082,943 B1
(45) Date of Patent: Aug. 1, 2006

(54) INHALER CASE COVER

(76) Inventor: Ametrice D. Clark, 20501 Trinity St., Detroit, MI (US) 48219

( * ) Notice: Subject to any disclaimer, the term of this patent is extended or adjusted under 35 U.S.C. 154(b) by 0 days.

(21) Appl. No.: 10/806,024

(22) Filed: Mar. 22, 2004

Related U.S. Application Data

(60) Provisional application No. 60/456,400, filed on Mar. 20, 2003.

(51) Int. Cl.
   *A61M 11/00*   (2006.01)
   *A61M 15/00*   (2006.01)
   *A45F 3/14*    (2006.01)
   *A45F 5/00*    (2006.01)

(52) U.S. Cl. ............... 128/200.23; 128/203.15; 224/250; 224/251

(58) Field of Classification Search ........... 128/200.23, 128/200.14, 203.15, 203.23, 200.12; 604/58; 224/250, 251, 254, 269, 271, 677, 148.6; D3/203.1; 222/173, 175
See application file for complete search history.

(56) References Cited

U.S. PATENT DOCUMENTS

| | | | |
|---|---|---|---|
| 4,220,263 A * | 9/1980 | Caruso ................... 222/183 |
| 4,454,966 A * | 6/1984 | Hicks ................... 222/153.11 |
| 5,002,214 A * | 3/1991 | Caranci ................... 224/669 |
| 5,287,995 A * | 2/1994 | Redman et al. ............. 222/175 |
| 5,392,975 A * | 2/1995 | Blankenship, Jr. ....... 224/148.5 |
| 5,458,263 A * | 10/1995 | Ciammitti et al. ....... 222/153.1 |
| 5,477,999 A * | 12/1995 | Blankenship, Jr. .......... 224/666 |
| 5,503,316 A * | 4/1996 | Stewart .................. 224/312 |
| 5,730,118 A * | 3/1998 | Hermanson ........... 128/200.14 |
| 5,779,122 A * | 7/1998 | Martinelli .................. 224/683 |
| 5,855,307 A * | 1/1999 | Biddick et al. ............. 224/267 |
| 5,899,200 A * | 5/1999 | McNary ................. 128/200.14 |
| 6,145,654 A * | 11/2000 | Loghman ..................... 206/37 |
| 6,164,275 A * | 12/2000 | Van Iderstine ......... 128/200.14 |
| 6,360,929 B1 * | 3/2002 | McCarthy ................... 224/251 |
| 6,557,737 B1 * | 5/2003 | Hanson .................. 224/148.6 |
| 6,685,068 B1 * | 2/2004 | Thompson et al. ......... 224/251 |
| 6,820,612 B1 * | 11/2004 | Harabin ................. 128/200.23 |

* cited by examiner

*Primary Examiner*—Teena Mitchell
(74) *Attorney, Agent, or Firm*—John R. Benefiel

(57) ABSTRACT

A cover for an inhalant case includes a tubular fabric portion closed at the top and open at the bottom to be able to receive an inhalant casing with an angled opening extending down on one side, sized to allow the casing spout to protrude therethrough. A cap hood is tethered on one side to an upper edge of the opening and configured to receive and retain a spout cap. A carrier strap is connected to the bottom edge of the tubular portion. The tubular portion may be constructed as a sleeve with a sewn hem, or openable by a hook and loop fasteners to be able to be wrapped and unwrapped on or off the casing.

5 Claims, 1 Drawing Sheet

INHALER CASE COVER

CROSS REFERENCE TO RELATED APPLICATIONS

This application claims the benefit of U.S. provisional Ser. No. 60/456,400, filed Mar. 20, 2003.

BACKGROUND OF THE INVENTION

This invention concerns inhaler and more particularly, cases or covers for inhalers. Asthma suffers often carry inhalers to be handy for use in case of an asthma attack. These consist of a replaceable pressurized canister of a medicament which is inserted in a casing having a tubular portion open at the bottom to receive the canister which is positioned with the aerosol plunger against the top of the casing. An angled spout extends laterally from the upper side of the tubular portion. When the protruding bottom of the canister is pushed up, the plunger is depressed and a spray is emitted confined and directed by the spout. The spout itself has a cap which is readily placed over the open end of the spout.

The inhalers must be kept handy when being carried for quick use, particularly by children in the event of an asthma attack.

Children are also often interested in making the inhaler more appealing in appearance since it is conspicuously carried as by a neck strap.

Various covers have heretofore been provided for these inhaler casings which provide an attachment or support.

The angled spout of the inhaler makes installing a cover over the inhaler case difficult. The spout cap also should desirably be secured lest it be lost after removing the same in preparation for use.

While tethered caps have been proposed, the securement of the cap to the strap and cover has not been convenient.

It is the object of the present invention to provide an attractive cover for an inhaler case which is easily installed and removed and also provides a convenient securement of the inhaler spout cap.

SUMMARY OF THE INVENTION

The above object and other objects which will be understood upon a reading of the following specification and claims are accomplished by a cover made from a moderately stretchable fabric material, including a tubular main section configured to receive and snugly fit to the body portion of the inhaler case. The bottom of the tubular main section is open to allow easy insertion of the case. A securement such as a ring and strap or ribbon passed through grommeted or hemmed openings in the material is attached to the lower portion of the tubular section.

At the top, an opening is formed inclined down along the upper part of one side of the tubular main section to allow the inhaler spout to protrude.

The tubular main section can thus stretch to accommodate the spout as the cover is pulled onto the case using the ring as a convenient pull, the spout then pushed out through the opening.

The tubular portion can also be of a wrap around design, secured with mating hook and loop elements to likewise be easily installed.

A stretchable fabric cap hood is also provided having one side sewn onto one side of the top of the opening therein which is sized to readily allow insertion of the inhaler spout cap and to be held therein to prevent loss of the cap.

The inhaler case and spout are thus completely enclosed except for the protruding bottom of the canister, presenting an attractive appearance.

Thus, an attractive, convenient to install inhaler cover is provided.

DETAILED DESCRIPTION

In the following detailed description, certain specific terminology will be employed for the sake of clarity and a particular embodiment described in accordance with the requirements of 35 USC 112, but it is to be understood that the same is not intended to be limiting and should not be so construed inasmuch as the invention is capable of taking many forms and variations within the scope of the appended claims.

Figure 1:
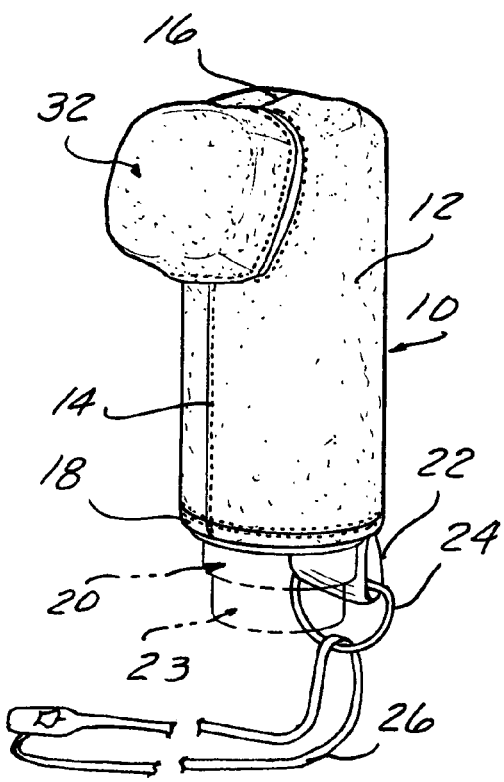
FIG. 1 is a pictorial view of a first embodiment of an installed inhaler cover according to the invention.
Figure 2:
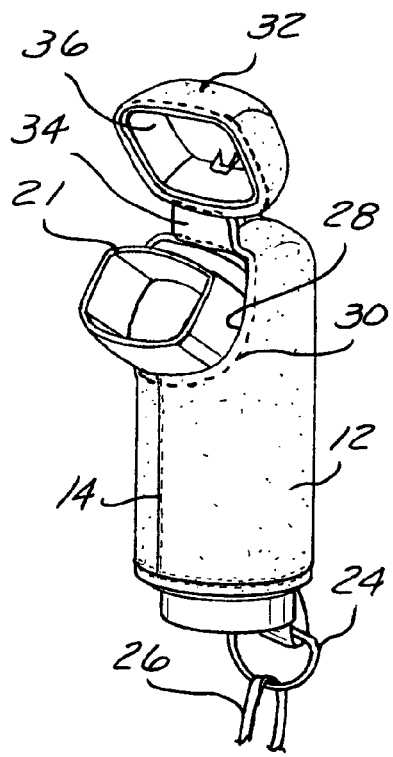
FIG. 2 is a pictorial view of the installed cover shown in FIG. 1 with the spout cap and cap hood hinged open.

Referring to the drawings and particularly FIGS. 1 and 2, the cover 10 includes a tubular main portion 12 which is constructed of a sleeve made of a moderately stretchable fabric material sewn together along a vertical seam 14 extending up from the bottom edge and seams 16 forming a closed upper end.

A hem 18 is sewn around the open lower end. A cylindrical inhalant casing lower portion 20 is enclosed by the cover tubular portion 12. The casing lower portion can receive a pressurized medicament canister 21.

A strap loop 22 is sewn into the hem 18 capturing a ring 24 through which a carrier strap 26 can be passed.

The main cover portion 12 has an inclined opening 30 extending down at an angle from its upper end around which is sewn a hem.

A cap hood 32 sized and positioned to selectively be fit over the opening 30, and is secured on its upper side to the upper edge of the opening 30 by a short strap 34.

The opening 30 is located and sized to allow the casing spout 21 to protrude therefrom.

The size and shape of the cap hood 32 is such as to allow insertion of the inhalant spout cap 36 which is thereafter retained therein.

Using the ring 24 as a grip it is easy to pull the cover 10 down over the inhalant casing 20 until the casing spout 21 reaches the opening 30, and allow protrusion of the casing spout 21 therethrough. The cap hood 32 is quickly emplaced over the cap 36 to complete the installation.

Figure 3:
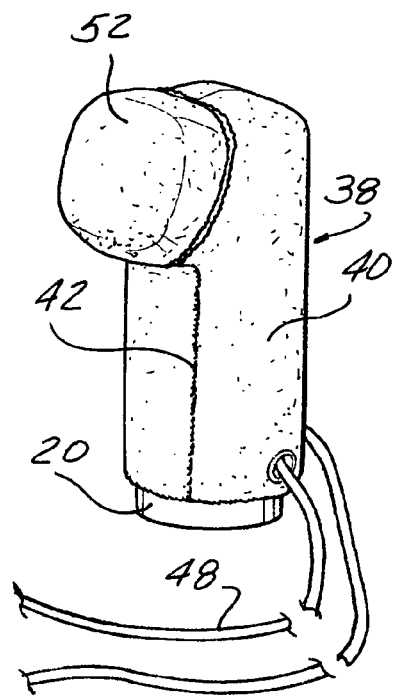
FIG. 3 is a pictorial view of a second embodiment of an inhaler cover according to the invention, using a wrapped tubular portion.
Figure 4:
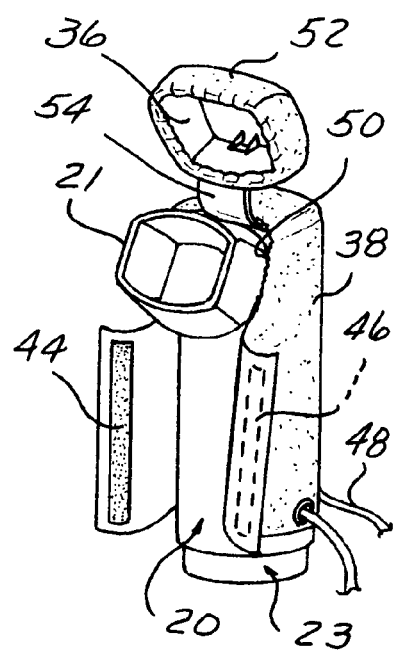
FIG. 4 is a pictorial view of the cover shown in FIG. 3, with the cap and cap hood hinged back and the tubular portion partially unwrapped.

FIGS. 3 and 4 show a second embodiment of a cover 38 according to the invention, which also includes a tubular main portion 40, which is wrapped around a canister 20 and secured along a separable seam 42 by strips 44, 46 of hook and loop fasteners.

A carrier strap or ribbon 48 is looped through openings near the lower edge of the tubular main portion 40.

A angled cutout 50 forms an opening when the tubular main portion 38 is wrapped onto the canister 20.

A cap hood 52 is tethered by a strap 54 sewn to the closed upper edge of the tubular portion 38. The inhalant cap 36 is received and retained in the hood 52.

Thus, the inhalant casing 20 is completely enclosed within the covering to present an attractive appearance, and the cap 36 is safely held when removed by flipping the cap hood 52 back.

At the same time, the cover 38 is readily installed onto the casing 20 without the use of adhesives or fasteners.

The invention claimed is:

1. A fabric cover for an inhalant casing of the type having a cylindrical part with an angled spout at the top thereof with a cap on said spout, said covering comprised of a tubular main portion of a stretchable fabric open at a lower end and closed at the upper end;

a downwardly angled opening extending down from the upper end of said tubular main portion;

said tubular main portion receiving and substantially enclosing said cylindrical part of said inhalant casing with said spout protruding through said opening;

a fabric cap hood sized to receive and retain said inhalant spout cap, said cap hood tethered on one side to an upper edge of said opening of said main portion to be held thereto so that said spout cap can be removed while being held in said cap hood and retained in said cap hood after said cap hood is swung away from said main portion on said tether.

2. The covering according to claim 1 wherein said main portion is held wrapped into said tubular shape with a hook and loop securement along a vertical seam.

3. The covering according to claim 1 further including a ring strap loop sewn into a bottom edge of said main portion with a ring held on said loop.

4. The covering according to claim 3 further including a carrier strap looped through said ring.

5. The covering according to claim 1 wherein a carrier strap is looped through one or more holes adjacent the bottom edge of said tubular portion.

* * * * *